United States Patent [19]
Jensen et al.

[11] Patent Number: 4,995,391
[45] Date of Patent: Feb. 26, 1991

[54] ELECTRODE DEVICE

[75] Inventors: Ole J. Jensen, Søborg; Steen G. Melberg, Bagsvaerd, both of Denmark

[73] Assignee: Radiometer A/S, Denmark

[21] Appl. No.: 821,872

[22] Filed: Jan. 24, 1986

Related U.S. Application Data

[63] Continuation of Ser. No. 727,191, Apr. 26, 1985, abandoned, which is a continuation of Ser. No. 451,141, filed as PCT DK82/00024 on Mar. 19, 1982, published as WO82/03275 on Sept. 30, 1982, abandoned.

[30] Foreign Application Priority Data

Mar. 20, 1981 [DK] Denmark ............................. 1252/81

[51] Int. Cl.$^5$ ................................................ A61B 5/14
[52] U.S. Cl. ................................. 128/635; 204/415; 204/433
[58] Field of Search ................ 128/635; 204/403, 415, 204/433

[56] References Cited

U.S. PATENT DOCUMENTS

| | | | |
|---|---|---|---|
| 3,445,363 | 5/1969 | Simon et al. | 204/420 |
| 4,012,308 | 3/1977 | Jerrold-Jones et al. | 204/433 |
| 4,324,256 | 4/1982 | Vesterager | 128/635 |

Primary Examiner—William E. Kamm
Attorney, Agent, or Firm—Bryan, Cave, McPheeters & McRoberts

[57] ABSTRACT

An electrode device for the determination of the partial pressure of $CO_2$, $Pco_2$, in particular an electrode device for transcutaneous determination of $Pco_2$.

The interior electrolyte of the electrode device is adapted to the exterior electrolyte in such a manner that the potential difference measured over the exterior reference electrode and the interior reference electrode is substantially temperature-independent with a temperature dependence for the $CO_2$ partial pressure determination in the range of $-1\%/°C. - +1\%/°C$.

The interior electrolyte preferably contains a pH-buffer system based on phenyl phosphonic acid.

14 Claims, 3 Drawing Sheets

ELECTRODE DEVICE

This is a continuation of U.S. application Ser. No. 727,191 filed Apr. 26, 1985, abandoned which is a continuation of U.S. application Ser. No. 451,141 filed as PCT DK82/00024 on Mar. 19, 1982, published as WO88/03275 on Sept. 30, 1982, now abandoned.

The present invention relates to an electrode device for determining the partial pressure of $CO_2$.

The direct measurement of the partial pressure of carbon dioxide, $P_{CO_2}$, by means of a $P_{CO_2}$ electrode was first described in the literature by Stow and Randall (Am. J. Physiol. 179, 678, 1954 and Arch. Phys. Med. 38, 646, 1957).

The design of modern $P_{CO_2}$ electrode devices, however, is primarily based on J. W. Severinghaus' work (Appl. Physiol. 13, 515, 1958).

In practice, $P_{CO_2}$ electrode devices are especially used in the clinical field, and they are partly used intervascularly in the so-called catheter electrodes, partly built into more or less automated apparatus for determining blood gasses such as ABL2 Acid-Base Laboratory (Radiometer A/S, Copenhagen) or BMS2 MKIII (Radiometer A/S, Copenhagen), and partly built into an electrode housing designed for being placed on the skin.

By measurement with an electrode device of the latter type, the so-called transcutaneous $P_{CO_2}$ value is obtained. A detailed description of a suitable electrode for determining the transcutaneous $P_{CO_2}$ value is given, inter alia, in the specification of DK Patent Application No. 1361/78 and patent applications claims priority therefrom, including U.S. Ser. No. 20.870 filed 15 Mar. 1979, now U.S. Pat. No. 4,324,256, DE Patent Application No. 29 11 343.7 and JP Patent Application No. 37651/1979.

Hence, the electrode device according to the invention is of the known type comprising an electrode housing, a $CO_2$-permeable membrane, a pH-sensitive measuring electrode arranged behind the membrane and having a measuring area which is in contact with a bicarbonate-containing exterior electrolyte placed between the measuring area and the membrane, and with an interior electrolyte and an interior reference electrode, and an exterior reference electrode in contact with the exterior electrolyte.

The principle of measurement with such an electrode device is that the electrolyte between the $CO_2$-permeable membrane and the pH-sensitive measuring electrode is equilibrated to a carbon dioxide concentration which is determined by Henry's law and which, hence, is proportional to the partial pressure of carbon dioxide outside the membrane, and the pH measured by the pH-sensitive measuring electrode will depend upon the ratio between carbon dioxide and bicarbonate in the electrolyte layer between the glass electrode and the membrane so that the measured pH is a function of the $P_{CO_2}$ outside the membrane.

Hence, in the exterior electrolyte system, the equilibrium:

$$CO_2 + H_2O \rightleftharpoons HCO_3^- + H^+$$

prevails, which, in view of Henry's law, results in:

$$pH_y = pK_y + \log \frac{HCO_3^-}{\alpha \cdot P_{CO_2}}$$

where $\alpha$ is the dissolution coefficient for $CO_2$, and $P_{CO_2}$ is the corresponding partial pressure. The activity coefficient is considered as being contained in the pK, and the suffix y refers to the exterior electrolyte system.

In practice, the bicarbonate concentration and $\alpha$ may be considered constant, and hence, the relationship between pH and $P_{CO_2}$ may simply be expressed as:

$$\log P_{CO_2} = \text{constant} - pH_y.$$

When a $P_{CO_2}$ electrode device according to the invention is brought into contact with a sample medium having a certain partial pressure of carbon dioxide, a potential difference $\Delta E$ will be present between the interior reference electrode and the exterior reference electrode. This potential difference will typically be temperature-dependent such as appears from the following example where it is presumed that both the exterior reference electrode and the interior reference electrode are constituted by the well-known Ag/AgCl electrodes.

In this case, the electrode chain is:

$$Ag/AgCl/Cl_i^-, pH_i // glass // pH_y, Cl_y^- /AgCl/Ag$$

If the total electrode chain is in equilibrium, the electromotoric power may be expressed as:

$$\Delta E = E_y - E_i = \frac{R'T}{F}\left[(pH_i - pH_y) + \log\frac{a(Cl_y^-)}{a(Cl_i^-)}\right] + (1)$$

$$E_{as} = \frac{R'T}{F}\left[(pK_i - pK_y) + \log\frac{[B]}{[A]} + \log\frac{\alpha \cdot P_{CO_2}}{[HCO_3^-]} + \log\frac{a(Cl_y^-)}{a(Cl_i^-)}\right] + E_{as}$$

where $a(Cl_y^-)$ and $a(Cl_i^-)$ designate the activity of $Cl^-$ in the exterior and the interior system, respectively, and $K_i$ is the dissociation constant for an acid/base pair A/B in the interior electrolyte.

$E_{as}$ is the asymmetry potential, defined as the potential measured over the glass membrane when the electrode chain is symmetrical with respect to the components present in the interior and exterior systems.

If it is presumed that $E_{as}$ is constant at a given temperature, it appears from equation (1) that the electrode chain gives a linear relationship between $\Delta E$ and $\log P_{CO_2}$ so that $$\Delta E = \frac{R'T}{F}(\log P_{CO_2} - \log k(T)) \qquad (2)$$

The value of $k$ (T) is derived from equation (1) in the following manner:

$$\log k(T) = pK_i - pK_y + \log B/A + \log\frac{\alpha}{[HCO_3^-]} + \log\frac{[Cl^-]_y}{[Cl^-]_i} \qquad (3)$$

ignoring the asymmetry potential, $E_{as}$.

The above expression incorporates the activity of the potential-controlling protolytes and ions on both sides of the glass electrode membrane as well as the three temperature-dependent parameters $pK_i$, $pK_y$ and $\alpha$.

In an electrode chain with an EMK-signal, $\Delta E$, which is temperature-dependent for a given $P_{CO2}$, it is evident that the EMK-signal obtained by a measurement or a calibration must be related to a specified temperature in order to be useful for delivering information about the $P_{CO2}$ in question.

Especially in the calibration situation where the EMK signal of the electrode device is correlated to a known $CO_2$ partial pressure in order to secure reproducible results in the subsequent measuring process, it is therefore important and also well-known that the calibration system will have to be subjected to an exact thermostating.

In the in vitro calibration of an electrode device for determining a gas partial pressure, the electrode device is placed in a calibration equipment and is subjected to well-defined temperature conditions in connection with a liquid or a gas having a well-defined partial pressure of the gas in question. In the measuring equipment, the electrode signal is correlated with to the known partial pressure of the calibration medium. In accordance with usual practice, one may choose between one point calibration and two point calibration.

When measuring with the electrode device where this is contacted with a medium having an unknown $CO_2$ partial pressure, the connected measuring equipment calculates the quantity of $P_{CO2},b$ on the basis of the electrode signal $\Delta E$ (EMK of the electrode device) from the calibration values and an algorithm coded into the measuring equipment. In the following, the designations $P_{CO2},b$, the $CO_2$ partial pressure determination, the $P_{CO2}$ determination or the calculated $CO_2$ partial pressure are used for the $CO_2$ partial pressure read out from the measuring equipment, whereas $P_{CO2}$ or $CO_2$ partial pressure is used for the true values.

For electrode devices of the type which give a temperature-dependent EMK signal it is necessary to aim at an exact thermostating, not only in the calibration, but also in connection with the measuring operation proper, and it has previously been specified for, e.g., transcutaneous electrode devices that these should be thermostated to an exactitude of $\pm 0.2°$ C., vide, e.g., the above-mentioned patent applications claiming priority from Danish Patent Application No. 1361/78.

According to the present invention, however, electrode devices for determination of the partial pressure of carbon dioxide are modified in such a manner that the EMK signal of the electrode device, $\Delta E$, becomes substantially temperature-independent at the normally occurring in vivo partial pressure of $CO_2$ (30–80 mm Hg). Such a modified electrode device is provided by the present invention, and this device is characterized in that the interior electrolyte is adapted to the exterior electrolyte in such a manner that the potential difference, measured over the interior reference electrode and the exterior reference electrode at in vivo $CO_2$ partial pressure, is substantially temperature-independent with a temperature dependency corresponding to a temperature dependency for the $CO_2$ partial pressure determination in the range from $-1\%/°C$. to $+1\%/°C$.

Thus, when used in connection with clinically occurring $P_{CO2}$ values, the electrode device according to the present invention gives a substantially temperature-independent EMK signal which may be expressed mathematically by stating that $$\left(\frac{\delta \Delta E}{\delta T}\right)_{P_{CO2}} = \left(\frac{\delta(E_y - E_i)}{\delta T}\right)_{P_{CO2}} = \left(\frac{\delta E_y}{\delta T}\right)_{P_{CO2}} -$$

$$\left(\frac{\delta E_i}{\delta T}\right)_{P_{CO2}} = 0$$

As mentioned above, it is evident that with respect to measuring exactitude an electrode device of this type is less critical with respect to the thermostating exactitude than the known electrode devices.

In practice, the resolution of the measuring equipment and the requirements to the exactitude of the transcutaneous $P_{CO2}$ measurement in the clinical situation will determine how far the temperature dependency of the potential difference or of the $CO_2$ partial pressure determination may be allowed to deviate from 0.

The resolution of the measuring equipment may typically be 1 mm Hg, and the exactitude which is required of the $P_{CO2}$ determination for clinical purposes may be set at $\pm 10\%$.

A resolution of 1 mm Hg corresponds to 3.3% at $P_{CO2}=30$ mm Hg and to 1.3% at $P_{CO2}=80$ mm Hg. The interesting temperature interval is 37°–45° C.; hence, the interval length is 8° C. If it is desired to ensure that the read-out of the measuring equipment is not influenced by temperature changes between the extremes of the interval, the change in $P_{CO2},b$ must numerically be smaller than 1 mm Hg/8° C.$=0.13$ mm Hg/°C. This corresponds to a temperature dependency of 0.4%/°C. at 30 mm Hg and 0.2%/°C. at 80 mm Hg.

If it is alternatively presumed that the complete acceptable uncertainty of the $P_{CO2}$ determination is due to the temperature dependency, it is found that the acceptable temperature dependency is in the range of $-10\%/8°$ C. — $+10\%/8°$ C. or $-1.3\%/°C$. — $+1.3\%/°C$.

On the basis of this, suitable limits for the temperature dependency of the $P_{CO2}$ determination are $-1\%/°C$. — $+1\%/°C$., and preferred limits are $-0.2\%/°C$. — $+0.2\%/°C$.

An interesting advantage of the electrode device according to the invention is that the user becomes able to vary his electrode temperature within the normal temperature range for transcutaneous measurements without having to recalibrate his electrode device in connection with each temperature shift.

In uncritical situations it will be desirable to use a low electrode temperature, inter alia to avoid damaging the patient's skin, whereas in critical situations it will be desirable to use a higher electrode temperature so that the blood supply to the measuring site is increased. Large changes in the $CO_2$ partial pressure, which may be an indication of the patients' failing heart/lung function, will, in contrast, quickly become apparent, irrespective of the site on which the transcutaneous electrode device is placed on the body.

A preferred embodiment of the electrode device according to the invention is characterized in that the temperature dependency of the potential difference passes 0 for $CO_2$ partial pressures in the upper end of the in vivo range, preferably $CO_2$ partial pressures $>60$ mm Hg.

The suitability of having the numerically smallest temperature dependency of the potential difference or EMK delivered by the electrode device in the upper end of the in vivo range will be understood on the basis of equation (2) from which it appears that the relationship between the EMK and the $CO_2$ partial pressure is logarithmic. In other words, the same change of the EMK will result in the same percentage change in the $CO_2$ partial pressure determination so that a certain change of the EMK will result in an almost 3 times greater change of the $CO_2$ value calculated in the measuring equipment for $CO_2$ partial pressures in the upper end of the in vivo range as compound $CO_2$ partial pressures in the lower end of the in vivo range.

Theoretically, the following relationship may be found between the desired $Pco_2$ $(=P')$ which gives a temperature independent electrode potential, and the above-described quantity $k(T)$.

It follows from equation (2) that:

$$\Delta E = \frac{R'T}{F}(\log Pco_2 - \log P') + \frac{R'T}{F}(\log P' - \log k(T)).$$

As $\Delta E$ is temperature-independent for $Pco_2 = P'$, it follows that:

$$\left(\frac{\delta \Delta E}{\delta T}\right)_{Pco_2 = P'} = \delta\left[\frac{R'T}{F}(\log P' - \log k(T))\right]/\delta T = 0 \quad (4)$$

By rearranging equation (4) and using equation (3), it further follows that:

$$\log \frac{P'}{k(T)} = T \cdot \frac{\delta \log k(T)}{\delta T} = T\left(\frac{\delta pK_y}{\delta T} - \frac{\delta pK_i}{\delta T} - \frac{\delta \log \alpha}{\delta T}\right) \quad (5)$$

If the requirements are made more strict, so that $k(T) = P'$, that is that as both the zero point of the electrode device ($\Delta E = 0$ mV) and the temperature dependency $$0\left(\frac{\delta \Delta E}{\delta T} = 0\right)$$

appear at $Pco_2 = P' = k(T)$, it follows that the condition becomes:

$$\frac{\delta pK_y}{\delta T} - \frac{\delta pK_i}{\delta T} - \frac{\delta \log \alpha}{\delta T} = 0 \quad (6)$$

In this case, a simple electrode system is obtained which for $Pco_2 = P'$ will give $\Delta E = 0$ mV independent of the temperature.

The changes in $pK_y$ and $\log \alpha$ may be calculated from table values, and the following applies for aqueous systems:

$$\frac{\delta pK_y}{\delta T} = -0.0025° \text{ C.}^{-1}$$

$$\frac{\delta \log \alpha}{\delta T} = -0.0095° \text{ C.}^{-1}$$

which gives in $\frac{\delta pK_i}{\delta T} = +0.0070°$ C.$^{-1}$

For an electrode device according to the invention and showing the additional feature that $\Delta E$ is 0 at an in vivo partial pressure of carbon dioxide, suitable pH buffer systems, therefore, must be selected among buffer systems which have a $\delta pK_i/\delta T$ value of the order of 0.0070°C.$^{-1}$.

Considering that in the calibration procedure of the measuring equipment to which an electrode device according to the invention pertains, one normally works with a calibration liquid or calibration gas having a known $Pco_2$, the composition of this calibration liquid or gas being defined by the supplier of the measuring system, it will be advantageous, for an electrode device of the above type, to recommend a calibration liquid or gas with the specified $Pco_2$ value which gives a potential difference 0, and in particular to use this calibration liquid or gas for one point calibrations of the electrode device, considering that it will be easy for the user to remember and set the calibration value in the measuring system.

In the case where $\Delta E$ is different from 0 for $Pco_2 = P'$ (the partial pressure of $CO_2$ at which $$\frac{\delta \Delta E}{\delta T} = 0),$$

equation (5) results in:

$$\frac{\log \frac{P'}{k(T)}}{T} = \frac{\delta pK_y}{\delta T} - \frac{\delta pK_i}{\delta T} - \frac{\delta \log \alpha}{\delta T} \quad (7)$$

For an interior liquid system having a specified value of $$\frac{\delta pK_i}{T}$$

equation (7) determines the relation $$\frac{P'}{k(T)},$$

or for specified requirements to this relationship, equation (7) determines the size of $$\frac{\delta pK_i}{\delta T}.$$

The selection of pH buffer systems which have $P'$ values in the range of 30–80 mm Hg, however, must still be performed experimentally.

It is especially preferred that the reference electrode is an Ag/AgCl electrode, which is well known per se. Such a reference electrode is suitable for constituting part of a thermostating system for the electrode device according to the invention as described in the specification of the above-mentioned patent applications claiming priority from Danish Patent Application No. 1361/78.

With such a reference electrode, a stable potential, $E_y$, is secured in that the exterior electrolyte contains chloride ions.

It is furthermore preferred that also the interior reference electrode is an Ag/AgCl electrode, and that the interior electrolyte contains chloride ions.

Furthermore, it is preferred to define the pH value in the interior electrolyte in a manner known per se by having the interior electrolyte contain a pH buffer system, cfr. above.

Experimentally, it has been found that a phenyl phosphonic acid buffer system is a suitable buffer system for use in the interior electrolyte of the electrode device according to the invention.

A buffer system of similar kind has previously been suggested as interior liquid in temperature-stable glass electrodes for pH measurement (U.S. Pat. No. 3,445,363) having a zero point at pH 7. This patent does not touch the problem involved in adapting the temperature dependency of an interior electrolyte to the temperature dependency of an exterior electrolyte.

A specific composition of the exterior electrolyte and the interior electrolyte ensuring that the temperature dependency of the potential difference measured over the exterior reference electrode and the interior reference electrode falls within the desired range is:

| | | |
|---|---|---|
| 0.5 | M phenyl phosphonic acid | interior electrolyte |
| 0.75 | M NaOH | |
| 0.01 | M KCl or NaCl | |
| 0.2 | M KHCO$_3$ | exterior electrolyte |
| 0.5 | M KCl | |
| | dissolved in glycerine p.a. | |

Further details concerning the electrode devices with this electrolyte combination are given in connection with the description of FIG. 3 and FIG. 4 and in Example 1.

The invention also relates to an electrode component for use in an electrode device for the determination of the partial pressure of $CO_2$, which electrode component is characterized by comprising a pH-sensitive measuring electrode, the interior electrolyte of which contains a pH buffer system based on phenyl phosphonic acid.

Finally, the invention also relates to an electrolyte for use as interior electrolyte in an electrode device for determining the partial pressure of $CO_2$, said electrolyte being characterized by containing a pH buffer system based on phenyl phosphonic acid.

The invention will now be further described with reference to the drawing, where FIG. 1 shows an electrode device according to the invention.

Figure 1:
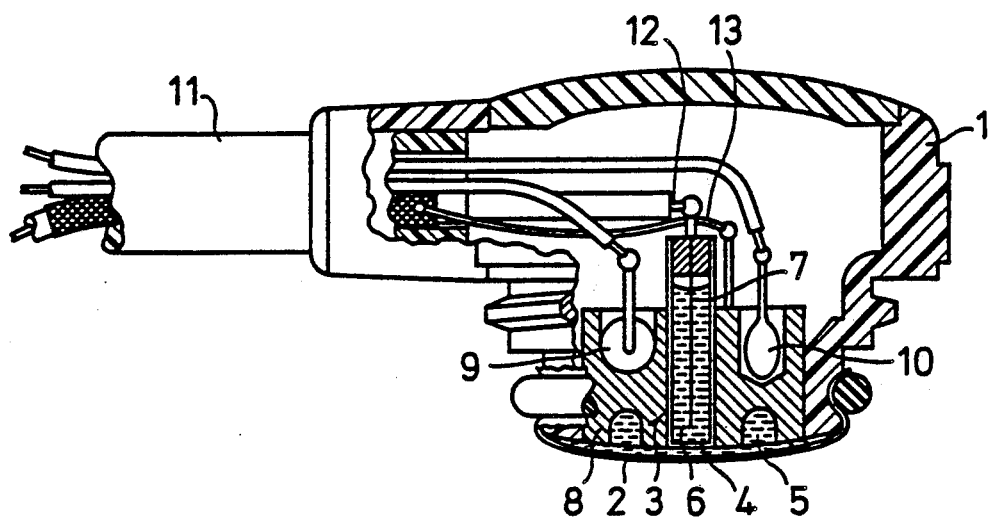

The electrode device shown in FIG. 1 is designed in a traditional manner for a transcutaneous $P_{CO2}$ electrode device. The electrode device comprises an electrode housing 1, a $CO_2$-permeable membrane 2, a pH-sensitive measuring electrode arranged behind the membrane, said electrode generally being designated 3 and having a measuring area 4 which is in contact with a bicarbonate-containing exterior electrolyte 5. The measuring electrode is embedded centrally in a silver body 8 which is chlorinated on its surface facing the membrane 2 and which constitutes the exterior reference electrode of the electrode device. The bicarbonate-containing exterior electrolyte 5 is placed in the space limited by the front surfaces of the electrode housing 1, the reference electrode 8, the measuring surface 4 and the membrane 2. The measuring electrode 3 has an interior electrolyte 6 and an interior reference electrode 7. The electrode device is thermostated by means of a Zener diode 9 and a thermistor 10, and the EMK value of the electrode device is read out via conductors 12, 13 in the electrode cable 11 connected with the measuring electrode 3 and the reference electrode 8, respectively.

According to the invention, the exterior electrolyte 5 and the interior electrolyte 6 are so adapted to each other that the temperature dependency of the EMK value is substantially 0. In the most preferred embodiment, the composition of the interior electrolyte is: 0.5M phenyl phosphonic acid, 0.75M NaOH and 0.01M KCl, and for the exterior electrolyte: 0.02M KHCO$_3$ and 0.5M KCl dissolved in glycerine p.a. (15% aqueous glycerine).

Figure 2:
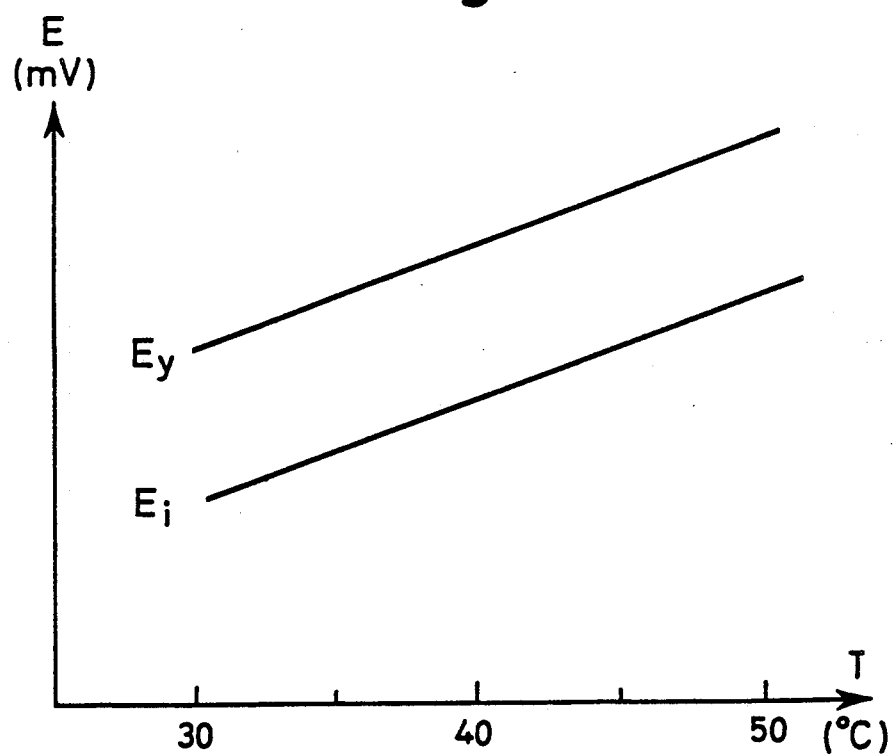
FIG. 2 shows the ideal course of the potentials for the interior electrolyte and the exterior electrolyte, respectively, as a function of the temperature.

FIG. 2 shows the course aimed at for the potentials of the interior electrolyte and the exterior electrolyte, respectively, as a function of the temperature at a fixed $CO_2$ partial pressure. As the two lines are parallel, it is evident that $$\left(\frac{\delta E_y}{\delta T}\right)_{P_{CO2}} - \left(\frac{\delta E_i}{\delta T}\right)_{P_{CO2}} = 0 \text{ or } \left(\frac{\delta \Delta E}{\delta T}\right)_{P_{CO2}} = 0$$

Figure 3:
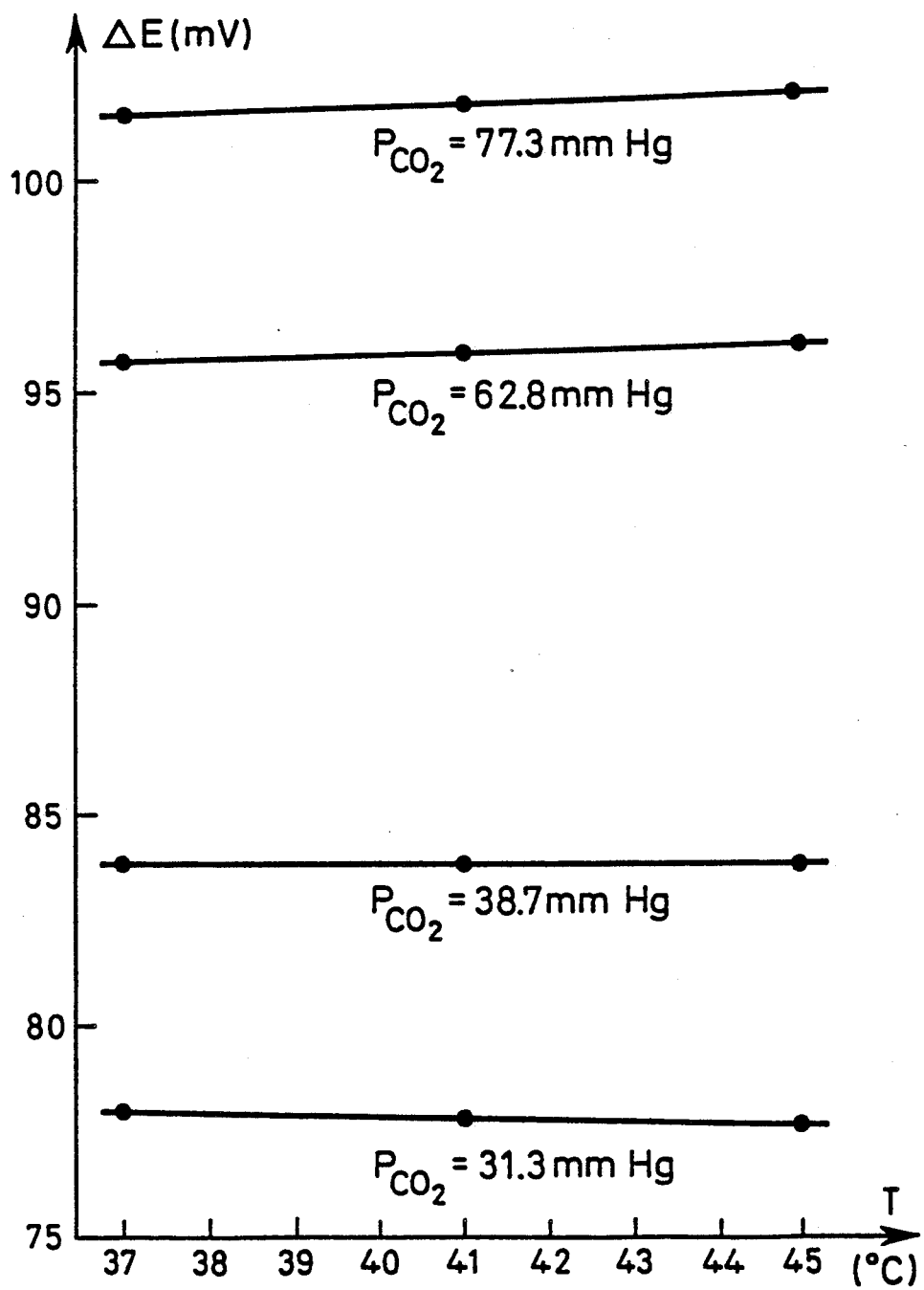
FIG. 3 and FIG. 4 show the EMK value as function of the temperature for an electrode device according to the invention for various partial pressures of $CO_2$ within the in vivo range.
Figure 4:
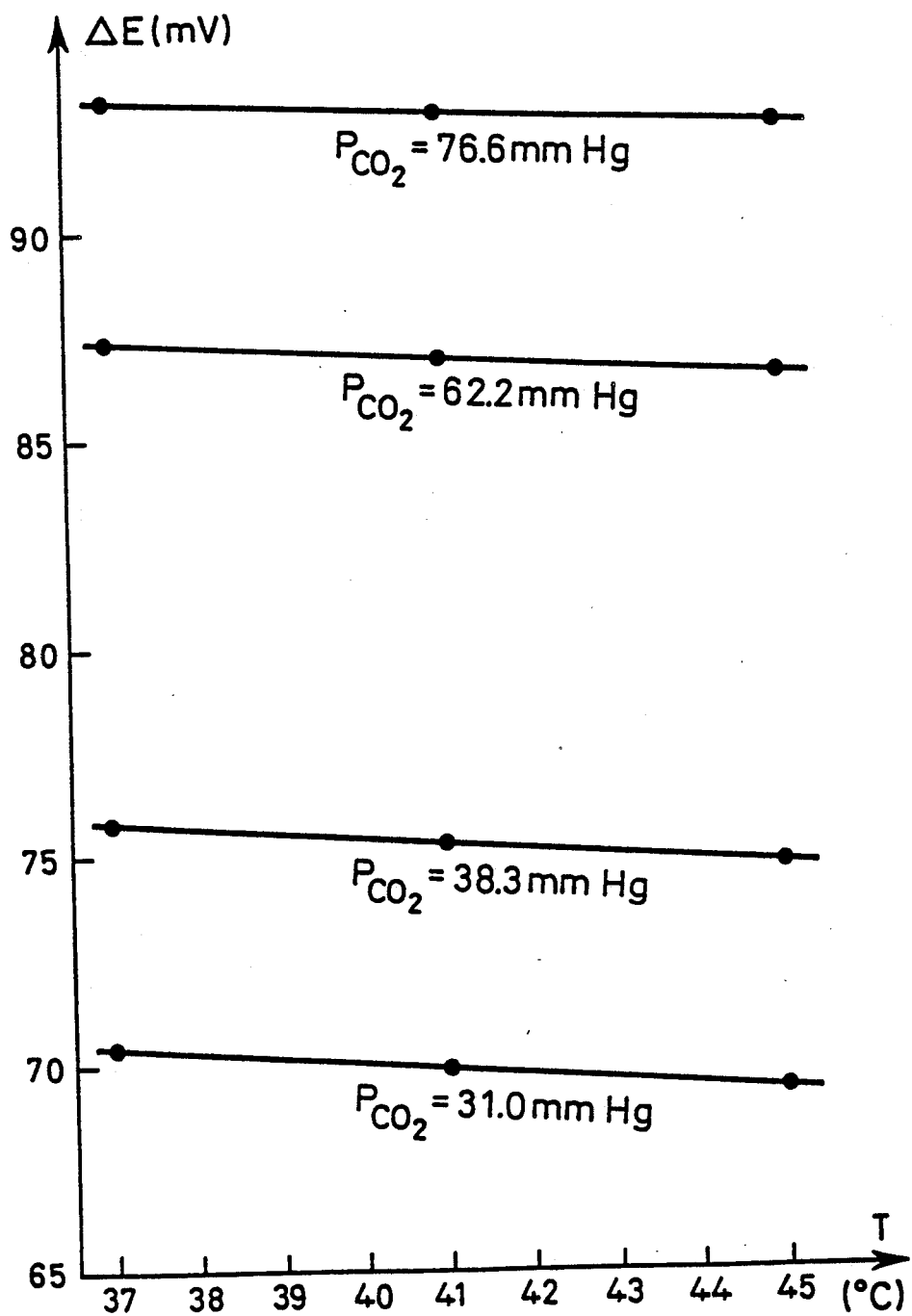

For two, in principle similar, electrode devices according to the invention, FIG. 3 and FIG. 4 show the course of the EMK, $\Delta E$, as a function of the temperature T.

In the two electrode devices, the composition of the exterior and the interior electrolyte, respectively, is as stated in the description of FIG. 1, and the electrode devices are designed as shown in FIG. 1.

It will be seen that $$\left(\frac{\delta \Delta E}{\delta T}\right)_{P_{CO2}}$$

for both electrode devices increases with increasing values of $P_{CO2}$.

From FIG. 3, it further appears that $$\left(\frac{\delta \Delta E}{\delta T}\right)_{P_{CO2}} = 0$$

is obtained for a $P_{CO2}$ around 40 mm Hg.

FIG. 3 is drawn on the basis of measurements with an electrode device which has been calibrated at 37° C. with 5.00% and 10.00% $CO_2$ in $N_2$ before the measurements. The results which form the basis for FIG. 3, and which comprise measurements on 4 $CO_2$ gas mixtures with known $CO_2$ content at three different temperatures, are stated in Table 1 below. The measuring results are partly stated in mV ($\Delta E$) and partly in mm Hg ($P_{CO2}$, b), parallel-coupled measuring equipment was used. The calculated $CO_2$ partial pressure was obtained on the basis of an algorithm coded into one of the measuring equipments (TCM10, Radiometer A/S) which expresses that the calculated $CO_2$ partial pressure is an exponential function of the potential difference $\Delta E$.

TABLE 1

| | 37.0° C. | | 41.0° C. | | 45.0° C. | |
|---|---|---|---|---|---|---|
| | Pco₂,b mm Hg | ΔE mV | Pco₂,b mm Hg | ΔE mV | Pco₂,b mm Hg | ΔE mV |
| 4.05 % CO₂ ~31.3 mm Hg | 31.5 | 78.0 | 31.3 | 77.8 | 31.1 | 77.6 |
| 5.00 % CO₂ ~38.7 mm Hg | 38.7 | 83.8 | 38.6 | 83.8 | 38.5 | 83.7 |
| 8.12 % CO₂ ~62.8 mm Hg | 61.8 | 95.7 | 62.2 | 95.9 | 62.5 | 96.0 |
| 10.00 % CO₂ ~77.3 mm Hg | 77.3 | 101.6 | 77.6 | 101.8 | 77.8 | 101.9 |

In the lower end of the in vivo range it is found that $$\left(\frac{\Delta\Delta E}{\Delta T}\right)_{31.3\ mm\ Hg} \sim \left(\frac{\delta\Delta E}{\delta T}\right)_{31.3\ mm\ Hg} =$$

$$\frac{77.6-78.0}{8}\ \frac{mV}{°C.} = -0.05\ \frac{mV}{°C.}$$

$$\left(\frac{\delta P_{co_2,b}}{\Delta T}\right)_{31.3\ mm\ Hg} \sim \frac{31.1-31.5}{8}\ \frac{mm\ Hg}{°C.} =$$

$$-0.05\ \frac{mm\ Hg}{°C.}$$

$$\left(\frac{\delta\ log\ P_{co_2,b}}{\Delta T}\right)_{31.3\ mm\ Hg} =$$

$$\frac{1}{P_{co_2}}\left(\frac{\delta P_{co_2}}{\delta T}\right) \sim -\frac{1}{31.3}\cdot 0.05\cdot 100\%/°C. = -0.16\%/°C.$$

In the upper end of the in vivo range it is found that $$\left(\frac{\delta\Delta E}{\delta T}\right)_{77.3\ mm\ Hg} \sim \frac{101.9-101.6}{8}\ \frac{mV}{°C.} = +0.038\ \frac{mV}{°C.}$$

$$\left(\frac{\delta P_{co_2,b}}{\delta T}\right)_{77.3\ mm\ Hg} \sim \frac{77.8-77.3}{8}\ \frac{mm\ Hg}{°C.} =$$

$$+0.063\ \frac{mm\ Hg}{°C.}$$

$$\left(\frac{\delta log\ P_{co_2,b}}{\delta T}\right)_{77.3\ mm\ Hg} \sim +\frac{1}{77.3}\cdot 0.063\cdot 100\%/°C. =$$

$$+0.08\%/°C.$$

Thus, the electrode device clearly fulfills the conditions stated in the main claim for the temperature dependency of the CO₂ partial pressure, according to which conditions this must be in the range −1%/° C.−+1%/° C. for Pco₂ values in the in vivo range.

FIG. 4 was drawn on the basis of measurements as described in connection with FIG. 3, with the exception that another electrode device was used for the measurements. The measuring results are stated in the Table 2.

TABLE 2

| | 37.0° C. | | 41.0° C. | | 45.0° C. | |
|---|---|---|---|---|---|---|
| | Pco₂,b mm Hg | ΔE mV | Pco₂,b mm Hg | ΔE mV | Pco₂,b mm Hg | ΔE mV |
| 4.05 % CO₂ ~31.0 mm Hg | 31.1 | 70.5 | 30.4 | 69.9 | 29.8 | 69.4 |
| 5.00 % CO₂ ~38.3 mm Hg | 38.3 | 75.8 | 37.4 | 75.3 | 36.6 | 74.8 |
| 8.12 % CO₂ ~62.2 mm Hg | 61.0 | 87.4 | 59.9 | 87.0 | 58.8 | 86.5 |
| 10.00 % CO₂ ~76.6 mm Hg | 76.6 | 93.2 | 75.4 | 92.9 | 74.2 | 92.5 |

It is observed that the reason why the same percentage content of CO₂ gives different CO₂ partial pressures (left column of Table 1 and Table 2) is that the measurements were performed at different barometer pressures.

In the lower end of the in vivo range it is found that $$\left(\frac{\delta\Delta E}{\delta T}\right)_{31.0\ mm\ Hg} \sim -0.14\ \frac{mV}{°C.}$$

$$\left(\frac{\delta P_{co_2,b}}{\delta T}\right)_{31.0\ mm\ Hg} \sim -0.16\ \frac{mm\ Hg}{°C.}$$

$$\left(\frac{\delta log\ P_{co_2,b}}{\delta T}\right)_{31.0\ mm\ Hg} \sim -0.5\%/°C.$$

In the upper end of the in vivo range it is found that $$\left(\frac{\delta\Delta E}{\delta T}\right)_{76.6\ mm\ Hg} \sim -0.088\ \frac{mV}{°C.}$$

$$\left(\frac{\delta P_{co_2,b}}{\delta T}\right)_{76.6\ mm\ Hg} \sim -0.30\ \frac{mm\ Hg}{°C.}$$

$$\left(\frac{\delta log P_{co_2,b}}{\delta T}\right)_{76.6\ mm\ Hg} \sim -0.3\%/°C.$$

Thus, also this electrode device is within the limits stated in the main claim for the temperature dependency of the determination of CO₂ partial pressures.

EXAMPLE 1

From a test series of electrode devices according to the invention designed as shown in FIG. 1 and having an exterior electrolyte of the following composition:
0.02M KHCO₃
0.5M KCl
dissolved in glycerine p.a.
and an interior electrolyte of the composition:
0.50M phenyl phosphonic acid
0.75M NaOH
0.01M NaCl
pH=6.84 (25° C.)
13 electrode devices were taken out, and their temperature coefficient determined by measuring on an 8.12% CO₂ gas mixture over the range of 37°–45° C.

The average temperature coefficient was determined to −0.17 mm Hg/° C. with a standard deviation of 0.18 mm Hg/° C. corresponding to a temperature coefficient at the CO₂ partial pressure in question (62.8 mm Hg) of $-0.27\%/°C$.

EXAMPLE 2

Presuming that for an electrode device according to the invention, $P'=60$ mm Hg, equation (4) gives:

$$\left(\frac{\delta\Delta E}{\delta T}\right)_{Pco_2=60 \text{ mm Hg}} = 0 \rightarrow$$

$$\frac{R'}{F}\log\frac{60}{k(T)} = \frac{R'T}{F}\frac{\delta\log k(T)}{\delta T}$$

For the lower end of the in vivo range it is found that $$\left(\frac{\delta\Delta E}{\delta T}\right)_{Pco_2=30 \text{ mm Hg}} = \frac{R'}{F}\log\frac{30}{k(T)} - \frac{R'T}{F}\frac{\delta\log k(t)}{\delta T} =$$

$$\frac{R'}{F}\log\frac{\frac{1}{2}\cdot 60}{k(T)} - \frac{R'T}{F}\frac{\delta\log k(T)}{\delta T} =$$

$$\frac{R'}{F}\log\tfrac{1}{2} + \frac{R'}{F}\log\frac{60}{k(T)} - \frac{R'T}{F}\frac{\delta\log k(T)}{\delta T} =$$

$$-\frac{R'}{F}\log 2 = -0.06 \text{ mV/°C}.$$

This corresponds to $$\left(\frac{\delta Pco_2,b}{\delta T}\right)_{Pco_2=30 \text{ mm Hg}} = -0.07 \frac{\text{mm Hg}}{°C}$$

$$\left(\frac{\delta\log Pco_2,b}{\delta T}\right)_{Pco_2=30 \text{ mm Hg}} = -0.2\%/°C.$$

For the upper end of the in vivo range it is correspondingly found that $$\left(\frac{\delta\Delta E}{\delta T}\right)_{Pco_2=80 \text{ mm Hg}} = +0.02 \text{ mV/°C}.$$

$$\left(\frac{\delta Pco_2,b}{\delta T}\right)_{Pco_2=80 \text{ mm Hg}} = +0.06 \text{ mm Hg/°C}.$$

$$\left(\frac{\delta\log Pco_2,b}{\delta T}\right)_{Pco_2=80 \text{ mm Hg}} = +0.1\%/°C.$$

It will be seen that these calculations are in line with the limits stated in the claims for the temperature dependency of the $Pco_2$ determination.

EXAMPLE 3

Electrode devices according to the invention may alternatively be prepared with an exterior electrolyte of the composition 0.005M NaHCO₃ and 0.2M NaCl in glycerine p.a. and an interior electrolyte of the composition 0.50M phenyl phosphonic acid, 0.75M NaOH and 0.01M NaCl or KCl.

We claim:

1. An electrode device for determining the partial pressure of $CO_2$ and comprising an electrode housing, a $CO_2$-permeable membrane, a pH-sensitive measuring electrode arranged behind the membrane and having a measuring area which is in contact with a bicarbonate-containing exterior electrolyte which is present between the measuring area and the membrane and having an interior electrolyte and an interior reference electrode, and an exterior reference electrode in contact with the exterior electrolyte, the interior electrolyte being so adapted to the exterior electrolyte that the potential difference measured over the exterior reference electrode and the interior reference electrode at in vivo $CO_2$ partial pressure is substantially temperature-independent with a temperature dependence corresponding to a temperature dependence for the $CO_2$ partial pressure determination in the range $-1\%/°C. - +1\%/°C$.

2. An electrode device according to claim 1, characterized in that the temperature dependence of the potential difference is 0 for a $CO_2$ partial pressure in the in vivo range.

3. An electrode device according to claim 2 in which the temperature dependence of the potential difference is an increasing function of $Pco_2$, and the temperature dependence of the potential difference passes 0 for $CO_2$ partial pressures in the upper range of the in vivo range, preferably $CO_2$ partial pressures $>60$ mm Hg.

4. An electrode device according to claim 1 wherein the potential difference is 0 at a specific $CO_2$ partial pressure in the in vivo range.

5. An electrode device according to claim 4 wherein the exterior electrolyte contains chloride ions in addition to bicarbonate.

6. An electrode device according to claim 5 wherein the reference electrode is an Ag/AgCl reference electrode.

7. An electrode device according to claim 6 in which the interior reference electrode is an Ag/AgCl electrode.

8. An electrode device according to claim 7 in which the interior electrolyte contains chloride ions.

9. An electrode device according to claim 8 in which the interior electrolyte contains a pH buffer system.

10. An electrode device according to claim 9 in which the pH buffer system is based on phenyl phosphonic acid.

11. An electrode device according to claim 9 in which the interior electrolyte comprises 0.5M phenyl phosphonic acid, 0.75M NaOH and 0.01M KCl or NaCl, and the exterior electrolyte comprises 0.02M KHCO₃ and 0.5M KCl.

12. An electrode device according to claim 11 in which the interior electrolyte comprises 0.5M phenyl phosphonic acid, 0.75M NaOH and 0.01M NaCl, and the exterior electrolyte comprises 0.005M NaHCO₃ and 0.2M NaCl.

13. An electrode device according to claim 12 in which the exterior electrolyte contains a glycol.

14. An electrode device according to claim 13 in which the glycol is glycerine.

* * * * *

UNITED STATES PATENT AND TRADEMARK OFFICE
CERTIFICATE OF CORRECTION

PATENT NO. : 4,995,391

DATED : February 26, 1991

INVENTOR(S) : Ole J. Jensen et al.

It is certified that error appears in the above-identified patent and that said Letters Patent is hereby corrected as shown below:

```
Column 1, Line 36:   Change "20.870" to --20,870--.
Column 5, line 13:   Change "compound" to --compared to--.
Column 11, Line 10:  Change "→" to -- = --.
```

Signed and Sealed this

Twentieth Day of April, 1993

Attest:

MICHAEL K. KIRK

Attesting Officer

Acting Commissioner of Patents and Trademarks